(12) United States Patent
Ley Vega De Seoane et al.

(10) Patent No.: US 7,122,315 B2
(45) Date of Patent: Oct. 17, 2006

(54) METHOD TO IDENTIFY ENVIRONMENTAL CONTAMINATION BY DETECTING ENTERIC VIRUSES

(75) Inventors: Victoria Ley Vega De Seoane, Madrid (ES); Miguel Angel Jimenez Clavero, Madrid (ES)

(73) Assignee: Instituto Nacional de Investigacion y Tecnologia Agraria y Alimentaria (INIA), (ES)

( * ) Notice: Subject to any disclaimer, the term of this patent is extended or adjusted under 35 U.S.C. 154(b) by 231 days.

(21) Appl. No.: 10/370,927

(22) Filed: Feb. 19, 2003

(65) Prior Publication Data
US 2004/0058312 A1    Mar. 25, 2004

(30) Foreign Application Priority Data
Feb. 19, 2002    (ES) ............................... 200200394

(51) Int. Cl.
*C12Q 1/68* (2006.01)
(52) U.S. Cl. ......................................................... 435/6
(58) Field of Classification Search ................... None
See application file for complete search history.

(56) References Cited

OTHER PUBLICATIONS

Castignolles, N., et al., "Detection of Adenovirus in the waters of the Seine River estuary by nested-PCR", *Molecular and Cellular Probes*, 12:175-180 (1998).
Pallin, R., et al., "The detection of enteroviruses in large volume concentrates of recreational waters by the polymerase chain reaction", *Journal of Virological Methods*, 67:57-67(1997).
Ley et al., "Bovine Enteroviruses as Indicators of Fecal Contamination", *Applied and Environmental Microbiology*, 3455-3461 (2002).
Wyn-Jones, A.P., et al., "Enteric viruses in the aquatic environment", *Journal of Applied Microbiology*, 91:945-962 (2001).
Muscillo, M., et al., "A New RT-PCR Method For The Identification Of Reoviruses In Seawater Samples", *Wat. Res.*, 35:548-556 (2001).
Knowles, N.J., et al., "A Serological Classification of Bovine Enteroviruses", *Archives of Virology*, 83:141-155 (1985).
Chapron, C.D., et al., "The detection of astrovirus in sludge biosolids using an integrated cell culture nested PCR technique", *Journal of Applied Microbiology*, 89:11-15 (2000).
Abbaszadegan, M., et al., "Detection of Enteroviruses in Groundwater with the Polymerase Chain Reaction", *Applied and Environmental Microbiology*, 1318-1324 (1993).
Abbaszadegan, M., et al., "A Strategy for Detection of Viruses in Groundwater by PCR", *Applied and Environmental Microbiology*, 444-449 (1999).

Bosch A., "Human enteric viruses in the water environment: a minireview", *Internal Microbiol*, 1:191-196 (1998).
Jiménez-Clavero, M.A., et al., "Teschoviruses as Indicators of Porcine Fecal Contamination of Surface Water", *Applied and Environmental Microbiology*, 69(No. 10):6311-6315 (2003).
Schvoerer, E., et al., "Qualitative and quantitative molecular detection of enteroviruses in water from bathing areas and from a sewage treatment plant", *Res. Microbiol.*, 179-186 (2001).
Zell R., et al., "Procine Teschoviruses Comprise at Least Eleven Distinct Serotypes: Molecular and Evolutionary Aspects", *Journal of Virology*, 1620-1631 (2001).
Zhang G., et al., "Molecular evolution of swine vesicular disease virus", *Journal of General Virology*, 80:639-651 (1999).
Vonsover, A., et al., "Identification of Feline- and Canine-Like Rotaviruses Isolated from Humans by Restriction Fragment Length Polymorphism Assay", *Journal of Clinical Microbiology*, 1793-1787 (1993).

Soule H., et al., "Monitoring Rotavirus Environmental Contamination in a Pediatric Unit Using Polymerase Chain Reaction", *Infection Control and Hospital Epidemiology*, 432-434 (1999).

Smith, A.W., et al., "Calicivirus-induced vesicular disease in cetaceans and probable interspecies transmission", *JAVMA*, 183(No. 11):1223-1225 (1983).

Lodder, W.J., et al., "Molecular Detection of Norwalk-Like Caliciviruses in Sewage", *Applied and Environmental Microbiology*, 5624-5627 (1999).

Hyypiä, T., et al., "Polymerase Chain Reaction for Human Picornaviruses", *J. gen. Virol.*, 70:3261-3268 (1989).

Reynolds, K.A., "Detection of Infectious Enteroviruses by an Integrated Cell Culture-PCR Procedure", *Applied and Enviromental Microbiology*, 1424-1427 (1996).

Abad, F.X., et al., "Astrovirus Survival in Drinking Water", *Applied and Environmental Microbiology*, 3119-3122 (1997).

*Primary Examiner*—Jeffrey Fredman
*Assistant Examiner*—Heather G. Calamita
(74) *Attorney, Agent, or Firm*—Ostrolenk, Faber, Gerb & Soffen, LLP

(57) ABSTRACT

The method consists of detecting an enteric virus in a test sample, where the detection of said enteric virus in said test sample indicates the existence of contamination. The method allows us to detect the presence or absence of enteric viruses in a test sample, and then to determine the existence of environmental contamination, especially faecal contamination of livestock origin, in the test sample and, therefore, the place where the test sample was taken. The characterisation and/or molecular or serological typification of the enteric virus detected and its comparison with that of other enteric viruses present in sources of contamination near to where the samples were taken for analysis, also allows us to identify the origin of said contamination.

26 Claims, 3 Drawing Sheets

METHOD TO IDENTIFY ENVIRONMENTAL CONTAMINATION BY DETECTING ENTERIC VIRUSES

FIELD OF THE INVENTION

The invention is related, in general, to the detection of organisms indicating environmental contamination, using enteric viruses as markers of faecal contamination of animal origin in order to determine the existence of environmental contamination, prevent human or animal infection and identify the origin of the contamination.

BACKGROUND OF THE INVENTION

The contamination of water and pastures can cause different diseases in the animals drinking the contaminated water and feeding on the pastures. The control of these possible sources of infection requires knowing if the pastures and water is contaminated in order to treat them accordingly, thus avoiding or reducing the risk of appearance of human or animal infections. The sources of such contamination include animal faeces, which may carry different organisms that could potentially contaminate the environment and/or pathogens affecting plants and animals, including humans.

Faecal microbiological contamination in water is usually analysed by determining the presence of organisms, not necessarily pathogenic, identified as "indicator or marker organisms". In this respect, some faecal bacteria, such as *Escherichia coli* have been used as faecal contamination markers (EP 438115 A2).

Surprisingly, it has now been discovered that enteric viruses, which infect the gastro-intestinal tract and are excreted in the faeces, can be used as environmental contamination markers, in particular, to identify faecal contamination of animal origin affecting pastures and water.

Enteric viruses form a heterogeneous group including representatives of different virus families, of which the most important are possibly picornaviruses (basically, enteroviruses and teschoviruses), caliciviruses, astroviruses and reoviruses (rotaviruses) and hepatitis E virus. In spite of their heterogeneity, these viruses have a series of characteristics in common, since they are nearly all small RNA viruses without a membranous envelope and stable in an acid pH (the only DNA virus in the group is the adenovirus). They can therefore withstand their route through the gastrointestinal tract, in the epithelium of which they usually establish acute infections, causing gastro-enteritis. They are disseminated through the faeces and transmitted through the faecal-oral route. Because of their characteristic resistance to adverse environmental conditions, they remain in the environment for long periods, and water contaminated by faeces and the food in contact with such water, mainly molluscs, are their primary transmission carriers.

Of the enteric viruses, one of the largest and best known groups is that of the enteroviruses, some of them important pathogens for humans and animals. Enteroviruses (EV) belong to the Picornaviridae family and their genome consists of a simple chain RNA positive pole molecule (ss-RNA+) with approximately 7,400 nucleotides (nt). These are the most common viruses and infect a large variety of mammals. Approximately 90 serotypes have been identified, 62 of which infect humans and 27 animals. Bovine enteroviruses (BEV) are broadly distributed all over the world and classified as enzootic in some countries. Two species have been described to date: BEV1 and BEV2 (Knowles, N. J., and Barnett, I. T. (1985), Arch Virol 83 (3–4), 141–55), although there are probably more that have not yet been identified. There are 3 species of porcine enteroviruses have been described. An ovine enterovirus (OEV-1) that is closely linked to the BEVs has been isolated. The existence of viruses has been described in ocean environments, although it is believes that most of the viruses found in natural water are cyanophages or other types capable of infecting microalgae. The existence of water contaminated by human enteric viruses has also been described, especially close to urban areas, related to sources of human infections [Chapron et al., 2000, Appl. Environ. Microbiol. 66:2520–2525; Abbaszadegan et al., 1993, Appl. Environ. Microbiol. 59:1318–1324; Abbaszadegan et al., 1999, Appl. Environ. Microbiol. 65:444–449; Bosch A., 1998, Int. Microbiol. 1:191–196; Pianetti et al., 2000, Epidemiol. Infect. 125:455–462; Schvoerer et al., Res. Microbiol. 152:179–186].

Another important group of porcine enteric viruses are Teschoviruses, related to enteroviruses (Zell, R., M. Dauber, A. Krumbholz, A. Henke, E. Birch-Hirschfeld, A. Stelzner, D. Prager, and R. Wurm. 2001. J Virol 75:1620–31) and including the agents causing both mild and severe forms of a neurological disease known as "Teschen-Talfan's disease", in addition to reproductive failure, pneumonia, diarrhoea and skin lesions in pigs. It is assumed in general that each animal species is the natural host of a large number of enteroviruses, often enzootic, and many of them probably pending identification. Although it is not common, they do occasionally transfer from one species to another, and this often gives rise to new emerging viral diseases. This appears to have occurred in the case of swine vesicular disease, an important swine disease caused by a human enterovirus which adapted to swine some 50 years ago (Zhang, G., D. T. Haydon, N. J. Knowles, and J. W. McCauley. 1999. Journal of General Virology 800:639–51).

Other enteric viruses, which are often found contaminating surface water, are reoviruses, in particular rotaviruses. Like enteroviruses, this virus group is very large. There are six known rotavirus antigen groups (groups A-F), infecting a wide range of species. Each group has its own preferences. For instance, group A viruses have been isolated in most of the mammal and bird species studied, group B viruses infect humans, pigs, cows, sheep and rats, group C infects pigs and rarely humans, and groups D and F are typical of birds, whereas group E is usually found in swine. They are stable in water and highly resistant to changes in temperature, pH and salinity. This carrier that contaminated water and the molluscs living in such water are important transmission carriers of these pathogens, both by their consumption and from contact when bathing or during other recreational activities (Bos, P., M. Kirsten, R. E. Cronje, and A. D. Steele. 1995. S Afr Med J 85:887–91., Bosch, A. 1998. Int Microbiol 1:191–6). Rotaviruses are highly variable, often giving rise to new reassortant variants when two different variants infect the same host. These natural reassortants, which can arise from different animal species, could play a role in the appearance of emerging human and animal diseases (Vonsover, A., I. Shif, I. Silberstein, H. Rudich, Y. Aboudy, E. Mendelson, L. Shulman, T. Nakagomi, and 0. Nakagomi. 1993. J Clin Microbiol 31:1783–7). Recently, Gratacap-Cavallier et al have detected human and bovine rotaviruses in potable water in the south-east of France, during an epidemic outbreak of viral diarrhoea in children (Gratacap-Cavallier, B., O. Genoulaz, K. Brengel-Pesce, H. Soule, P. Innocenti-Francillard, M. Bost, L. Gofti, D. Zmirou, and J. M. Seigneurin. 2000. Appl Environ Microbiol 66:2690–2). The co-detection of pathogenic human and animal viruses in potable water suggests a possible zoonosis in this outbreak, with water acting as the source of propagation.

Astrovirus infections are considered to be emerging viral diseases. Like other enteric viruses, they are transmitted in faeces/orally and are very persistent in aquatic media. Outbreaks are associated to the consumption of molluscs contaminated with waste water, and the intake of water contaminated by faeces. Besides in humans, astrovirus strains have been isolated from different animal species, including cows, sheep, swine, cats, dogs, ducks and turkeys (Abad, F. X., R. M. Pinto, C. Villena, R. Gajardo, and A. Bosch. 1997. Appl Environ Microbiol 63:3119–22. Chapron, C. D., N. A. Ballester, and A. B. Margolin. 2000. J Appl Microbiol 89:11–5).

Caliciviruses are well-known viral diarrhoea agents in many species, including humans, cats, pigs, cows and minks, and also in a large number of marine mammals, which apparently act as natural reserve stores (Smith, A. W., D. E. Skilling, N. Cherry, J. H. Mead, and D. O. Matson. 1998. Emerg Infect Dis 4:13–20., Smith, A. W., D. E. Skilling, and S. Ridgway. 1983. J Am Vet Med Assoc 183:1223–5). They are divided into five strains, of which four (Sapporo, Norwalk, hepatitis E and marine caliciviruses) are well-known pathogenic agents in humans. Many of these diseases can be considered cases of zoonosis, and species transfers are not uncommon, as can be seen with the swine disease known as swine vesicular exanthema, caused by a calicivirus that can not be distinguished from the San Miguel Sea Lion virus (Smith, A. W., D. E. Skilling, and S. Ridgway. 1983. J Am Vet Med Assoc 183:1223–5). Outbreaks of gastro-enteritis caused by caliciviruses are associated to the consumption of water contaminated with faecal waste and bathing in contaminated water (Lodder, W. J., J. Vinje, R. van De Heide, A. M. de Roda Husman, E. J. Leenen, and M. P. Koopmans. 1999. Appl Environ Microbiol 65:5624–7). Furthermore, there is increasing evidence that hepatitis E, caused by a virus that is closely liked to caliciviruses, could be of a zoonotic nature, because this virus is also pathogenic in several animal species, both domestic and wild, and it is found serologically in a growing number of animals, including pigs (Balayan, M. S. 1997. J Viral Hepat 4:155–65).

Finally, the adenovirus group, also a virus of between 60 and 90 nm with no membranous envelope, which makes it stable in ambient conditions, has a double DNA chain genome. Although this virus is not characteristic of gastrointestinal infections, it can have similar symptoms, such as gastro-enteritis, and be excreted in the faeces of infected individuals. It is often found contaminating water and molluscs (Pina, S., M. Puig, F. Lucena, J. Jofre, and R. Girones. 1998. Appl Environ Microbiol 64:3376–82).

Breakthroughs in molecular biology techniques have led to highly sensitive and specific RT-PCR protocols (reverse transcription-polymerase chain reaction) with better performances than classical isolation methods for the detection of enteric viruses with an RNA genome such as enteroviruses. Besides being highly sensitive, RT-PCR reactions provides an ADN fragment that can be sequenced and used to typify the isolated virus. Detection generally uses specific RNA region indicators containing conserved motives shared by this group of viruses (Hyypia et al., 1989, J. Gen. Virol. 70:3261–3268; De León et al., 1990, Pro. 1990 Amer. Water Works Assoc. WQTC; Reynolds et al., 1996, Appl. Environ. Microbiol. 62:1424–1427; Puig et al., 1994, Appl. Environ. Microbiol. 60:2963–2970; Schwab et al., 1995, Appl. Environ. Microbiol. 61:531–537).

SUMMARY OF THE INVENTION

Since there are enteric viruses infecting animals, generally in the form of an asymptomatic infection, which are excreted in their faeces, their possible use has been studied as environmental contamination markers, and in particular, as markers of faecal contamination of animal origin, in order to confirm the existence of environmental contamination, prevent human or animal infection and identify the origin of the contamination.

Therefore, in a particular embodiment, the prevalence and genotype of BEV has been studied in a closed herd of bovine livestock, and it has been compared with the virus found in animals sharing their close environment and environmental specimens. BEV was found in the faeces of most of the bovine livestock, and in environmentally close animals sharing the same pastures, and in the water obtained from the animals' drink tanks, pasture water, running water in the pastures and the river crossing the pastures. BEV was also found in the bay in which the rivers and streams crossing the pastures end (see Example 1 accompanying this description). We therefore evaluated the possibility of these viruses being used as a marker of the faecal contamination on a bovine livestock farm. The analysis of partial sequences of the viral genomes indicates that the same BEV variants were found both in the animals and in the contaminated areas. These results showed that this method can be used to identify the origin of environmental contamination and to conduct epidemiological studies on viral molecular evolution.

Recently, this study has been extended to several different locations in Spain confirming the BEV suitability as bovine livestock faecal waste marker, since this has been observed as endemic and has been found as contamination elements in surface waters near to the farms.

The use of enteric viruses from the teschovirus group as markers of contamination from waste of porcine origin has recently been validated by the applicants, showing that the detection method for this type of virus is extremely sensitive and specific, and capable of detecting waste disposal in a river several kilometres downstream. The test was performed including a parallel physical-chemical analysis of the water samples affected (Example 2). The results showed a good correlation between the data from the two types of analysis, with the porcine enteric virus detection method considerably more sensitive than the physical and chemical tests.

BRIEF DESCRIPTION OF THE FIGURES

FIG. 2 shows the variability between the BEV sequences from different sources and the most related serotypes. PS 87 is the sequence deposited in EMBL (access number X79368). RM2 is a serotype 2 BEV (EMBL access number X79369). VG 527 is a serotype 1 BEV (EMBL access number D00214). C+ corresponds to the sequence of the isolated BEV PS 87 obtained from the ATCC (catalogue number VR-774), used in this invention as a positive control. C corresponds to bovine faecal extracts. WF and WI correspond to water samples taken from Wye farm and the springs, respectively. D corresponds to deer faeces samples and G to goose faeces. O corresponds to oysters (stomach) and OP to an oyster gill wash pool. The asterisk (*) corresponds to a deleted nucleotide. The changes in nucleotides that are shared by all the isolated viruses are in bold type.

DETAILED DESCRIPTION OF THE INVENTION

The invention is related, in general, to the use of enteric virus as environmental contamination indicator (markers) organisms, in particular as markers of faecal contamination of animal origin in the environment, such as in water, pastures, etc. In a specific embodiment, this environmental contamination is faecal contamination of livestock origin, e.g. bovine, porcine, etc.

As it is used in this description, the term "enteric virus" includes all viruses infecting the gastro-intestinal tract and excreted in the faeces. The most important in relation to this issue are: enteroviruses, teschoviruses, rotaviruses, astroviruses, caliciviruses, hepatitis E virus and adenoviruses (Bosch, A., R. M. Pinto, and J. Jofre. 1988. Zentralbl Bakteriol Mikrobiol Hyg [B] 186:273–7., Gratacap-Cavallier, B., O. Genoulaz, K. Brengel-Pesce, H. Soule, P. Innocenti-Francillard, M. Bost, L. Gofti, D. Zmirou, and J. M. Seigneurin. 2000. Appl Environ Microbiol 66:2690–2., Knowles, N. J., and I. T. Barnett. 1985. Arch Virol 83:141–55., Ley, V., J. Higgins, and R. Fayer. 2002. Appl Environ Microbiol 68:3455–61., Lodder, W. J., J. Vinje, R. van De Heide, A. M. de Roda Husman, E. J. Leenen, and M. P. Koopmans. 1999. Appl Environ Microbiol 65:5624–7., Pina, S., M. Puig, F. Lucena, J. Jofre, and R. Girones. 1998. Appl Environ Microbiol 64:3376–82., Schwab, K. S., and R. D. Shaw. 1993. Baillieres Clin Gastroenterol 7:307–31., Vonsover, A., I. Shif, I. Silberstein, H. Rudich, Y. Aboudy, E. Mendelson, L. Shulman, T. Nakagomi, and O. Nakagomi. 1993. J Clin Microbiol 31:1783–7), etc.

In one aspect, the invention is related to a method to confirm the existence of environmental contamination, consisting of detecting the presence of an enteric virus in a test sample, in which the detection of such an enteric virus in such a test sample indicates the existence of environmental contamination. The molecular characterisation and/or typification of the enteric virus detected and its comparison with other enteric viruses present in sources of contamination close to where the samples were taken allows us to identify the origin of such contamination.

More specifically, the invention provides a method to identify the existence of faecal contamination of animal origin, for example bovine or porcine or from other species, consisting of detecting the presence of a enteric virus in a test sample, in which the detection of such enteric virus in such a test sample indicates the existence of faecal contamination of animal origin, bovine or porcine, for instance. The molecular characterisation and/or typification of the enteric virus detected and its comparison with other enteric viruses present in sources of contamination close to where the samples were taken allows us to identify the origin of such contamination.

Enteric viruses can be detected by any conventional method for the detection and identification of such viruses. Nevertheless, in a particular embodiment, the detection of such enteric viruses is performed by means of an enzymatic amplification reaction, for example by PCR (for viruses with a DNA genome, like adenoviruses) or RT-PCR (in most enteric viruses) on a region of the viral genome and the analysis of its nucleotide sequence. Therefore, in a particular embodiment, the invention provides a method for confirming the existence of environmental contamination caused by faecal waste of animal origin, by detecting an enteric virus in a test sample, which acts as a marker of such contamination, consisting of:

a) taking a test sample for which we desire to identify the existence of environmental contamination by detecting an enteric virus;

b) treating such a test sample in conditions allowing us to release and extract nucleic acid from the viral particles of enteric viruses eventually present in such a test sample;

c) enzymatically amplifying a sequence of target nucleotides present in the genome of such an enteric virus to obtain an amplification product; and d) analysing said amplification product to confirm the presence in or absence from the test sample of said enteric virus with the selected target sequence, where the detection of said enteric virus in said test sample indicates the existence of environmental contamination caused by faecal waste of animal origin.

The method provided by this invention starts with taking the test sample. The test sample can be taken from anywhere susceptible to contain animal enteric viruses, for example enteroviruses, teschoviruses, etc. for which we wish to identify the existence or not of environmental contamination, for example, caused by faecal waste of livestock origin (bovine, porcine, etc.). For instance, such a test sample can be taken from livestock facilities, livestock drinking water, the surrounding environment (pastures, water, etc.), from environmental specimens, from aquatic media in direct or indirect contact with the source of contamination, for example, effluents of the livestock facility containing livestock waste, rivers close to the source of contamination or crossing the possible source of contamination, etc. The source of contamination may be, for example, a livestock facility, typically a bovine or porcine livestock farm.

The test sample can be any sample susceptible to contain an enteric virus, for example, a teschovirus, since they are especially ideal to identify the existence of environmental contamination caused by faecal waste of porcine origin; or other enteric viruses such as enteroviruses, rotaviruses, caliciviruses, astroviruses, hepatitis E, adenoviruses, etc., which are suitable for identifying the existence of environmental contamination caused by faecal waste of bovine, porcine or other animal origin. For instance, said test sample can be a biological sample, such as a sample of an animal's faeces, a sample of animal tissues or cells, etc., or an environmental sample such as an environmental specimen, a sample of pasture, a water sample, a sample of fish or molluscs found in potentially contaminated water, etc.

The test sample is then subject to an appropriate treatment to remove the nucleic acid contained in the viral particles eventually present in said test sample.

In a particular embodiment, said viral particles are viral particles of enteric viruses with the RNA genome, for example Picornaviruses (basically, Enteroviruses and Teschoviruses), Caliciviruses, Astroviruses and Reoviruses (Rotaviruses) and hepatitis E virus. The RNA is extracted by conventional methods, using conventional kits and reagents (see Example 1, Materials and Methods section) and then placed in contact with the reagent for the reverse transcription (RT) reaction and for the polymerase chain reaction (PCR) in conditions in which a sequence of target nucleotides present in the genome of said enteric virus with an RNA genome is amplified to form an amplification product. The RT-PCR reaction can be performed using conventional methods, either in a single stage or in two stages. Experts on the subject are familiar with both alternatives. Depending on the alternative chosen, the reagent mix will contain one or other reagents, as explained later.

The reagent mix to perform the RT of the RNA of an enteric virus contains the reagents required for said reaction, for example water, dNTPs (dATP, dCTP, dGTP and dTTP), an appropriate buffer for the RT reaction, a reverse transcriptase, an initiator oligonucleotide which blends with a region of the RNA of the enteric virus in question and then, thanks to the reverse transcriptase, allows us to obtain a DNA complementary (cDNA) to said RNA, etc. On the other hand, the reagent mix for the PCR contains the reagents required for said reaction to take place, for example water, dNTPs, an appropriate buffer for the PCR reaction, a heat-stable polymerase DNA, a couple of initiators to amplify the target sequence of the genome of the enteric virus in question, a magnesium salt, etc. In a specific embodiment, said enteric virus is an EV, for example BEV, PEV, etc. In another specific embodiment said enteric virus is a teschovirus.

In a specific embodiment, the method provided by this invention is performed using a single RT-PCR reagent mix containing the reagents required for said reaction to take place, for example water, dNTPs, an appropriate buffer for the RT-PCR reactions, a reverse transcriptase, a heat-stable polymerase DNA, etc. There are kits available on the market that provide this reaction mix, to which the appropriate initiators are added. In this case, it is an advantage that the initiator used for the RT reaction is one of the initiators involved in the enzymatic amplification reaction (PCR).

To apply the method provided by this invention any initiator that allows us to obtain a cDNA of the enteric virus in question can be used, and any couple of initiators that allows us to amplify a target sequence of the genome of the enteric virus in question. In a specific embodiment, the enteric virus is an EV, such as a BEV, and the initiator used to obtain a BEV cDNA is one of the couple of initiators used to amplify a target sequence of the BEV cDNA. For instance, such indicators are specific to RNA regions containing preserved motives shared by EV. In a specific embodiment, said initiators are the initiators identified in this description as SEQ ID NO: 1 and SEQ ID NO: 2, which amplify a fragment of 183 base pairs (bp) containing part of the 5'-terminal end of the BEV RNA. In another specific embodiment, the enteric virus is a teschovirus and was detected by RT-PCR in real time using a marked Taqman probe the nucleotide sequence of which is as identified in SEQ ID NO: 3 and the initiators identified as SEQ ID NO: 4 (forward) and SEQ ID NO: 5 (reverse), amplifying a highly conserved non-coding 5' region of teschovirus.

Conventional techniques are used for the RT-PCR reaction (see the Example accompanying this description), in conditions in which an amplifiable DNA fragment, eventually present in the reaction medium, representative of a target sequence of an enteric virus, is amplified to form an amplification product. The amplification product is separated and analysed using conventional techniques, for example by electrophoresis, and sequenced, and we then identify the presence or absence in said test sample of an enteric virus containing the selected target sequence and identify the viral isolate. The identification of the isolate of the enteric virus(es) detected can be by conventional methods, for example by sequencing the region of the amplified viral genome. The detection of an enteric virus in said test sample indicates the existence of environmental contamination, in particular, faecal contamination of animal, for example livestock, origin. In a specific embodiment, the enteric virus with an RNA genome is an EV, for example BEV or PEV, the products of the RT-PCR reaction are separated by electrophoresis in agarose and viewed by conventional methods, for example ultraviolet light after staining with ethidium bromide. In another specific embodiment, the enteric virus with DNA genome is a teschovirus, the detection of the virus is made by real time RT-PCR using a Taqman probe.

In another specific embodiment, said viral particles are viral particles of enteric viruses with DNA genome, for example, adenoviruses. DNA is extracted using conventional methods based on conventional kits and reagents (Ley, V., J. Higgins, and R. Fayer. 2002. Appl Environ Microbiol 68:3455–61) and it is then placed in contact with the reaction mix for the polymerase chain reaction (PCR) in conditions in which a sequence of target nucleotides present in the genome of said enteric virus with DNA genome is amplified to form an amplification product. Conventional methods can be used for the PCR reaction, either in a single stage or in two stages. Experts on the subject are familiar with both alternatives. Depending on the alternative chosen, the reaction mix will contain one reagent or another, as explained later.

The reaction mix for the PCR contains the reagents required for said reaction, for example water, dNTPs, an appropriate buffer for the PCR reaction, a heat-stable polymerase DNA, a couple of initiators to amplify a target sequence of the genome of the enteric virus in question, a magnesium salt, etc.

Conventional techniques are used for the PCR, in conditions in which an amplifiable DNA fragment, eventually present in the reaction medium, representative of a target sequence of an enteric virus is amplified to form an amplification product. The amplification product is separated and analysed using any conventional method, for example by electrophoresis, and sequenced, and we then identify the presence or absence in said test sample of the enteric virus containing the selected target sequence and identify the viral isolate. The identification of the isolate of the enteric virus (es) detected can be by conventional methods, for example by sequencing the region of the amplified viral genome. The detection of an enteric virus in said test sample indicates the existence of environmental contamination, in particular, faecal contamination of animal, for example livestock, origin. In a specific embodiment, the products of the RT-PCR reaction are separated by electrophoresis in agarose and viewed by conventional methods, for example ultraviolet light after staining with ethidium bromide.

The method provided by this invention allows us to detect the presence or absence of enteric viruses, for example teschoviruses, enteroviruses, etc., in a test sample and then determine the existence of environmental contamination, for example, faecal contamination of animal, in particular livestock (bovine, porcine, etc.) origin in the test sample and, consequently, in the place from which the test sample was taken. The molecular characterisation and/or typification (DNA sequencing and analysis of sequences) of the enteric virus detected and its comparison with that of the other enteric viruses present in sources of contamination close to where the samples were taken for analyses also allows us to identify the origin of said faecal contamination. In a specific embodiment, said enteric virus is an EV whereas in another specific embodiment, said enteric virus is a teschovirus (see the Example accompanying this description).

The method provided by this invention can be used in different applications, for instance to identify the existence of environmental contamination, such as the identification of faecal contamination of animal, for example livestock (bovine, porcine, etc.) origin, to discover the origin of said contamination, to conduct epidemiological studies or studies related to viral molecular evolution, etc.

In another aspect, the invention provides a method to discover the origin of a source of environmental contamination, such as a source of faecal contamination of animal, for example livestock (bovine, porcine, etc.) origin, consisting of detecting an enteric virus, for example a teschovirus, enterovirus, etc., in a test sample according to the aforementioned method, and the comparison of the enteric viruses eventually detected in said test sample with other enteric viruses isolated and characterised in different possible sources of contamination, where the existence of a certain degree of identify between the isolated of the enteric viruses detected and characterised in said test sample and the isolated of enteric viruses found in a possible source of contamination indicates that said possible source of contamination is a source of environmental contamination, in particular, the source of faecal contamination of animal (bovine, porcine, etc.) origin.

In another aspect, the invention provides a method to control the dissemination of outbreaks of infections caused by enteric viruses, for example, such as the outbreak of foot and mouth disease in the United Kingdom in 2001, or classic swine fever in Catalonia from 2000 to 2002, or vesicular swine disease, which has been present in Italy for decades.

As it is used in this description, the expression "certain degree of identity" means that the identity between the isolates of the enteric viruses detected and characterised in said test sample and the isolates of the enteric viruses found in said possible source of contamination is 50% or more, preferably 80% or more, and more preferably 95% or more, when said degree of identity is measured by molecular sequencing of the region of the viral genome used in this study. If another less conserved region of the genome of an enteric virus is used, these values could be somewhat different. Alternatively, other techniques may be used, for example molecular typification, serological, etc., allowing us to compare the isolates of enteric viruses and conclude that two isolates of different enteric viruses belong to the same genotype or serotype.

The invention could be materialised in a kit for the detection of enteric viruses, for example, picornaviruses (basically teschoviruses and enteroviruses), reoviruses (in particular rotaviruses), astroviruses, caliciviruses, hepatitis E virus, adenoviruses, etc., as markers of environmental contamination, in particular, as markers of faecal contamination of animal, for example livestock (bovine, porcine, etc.), origin by enzymatic amplification, consisting of (a) when the enteric virus to be detected is an enteric virus with DNA genome, for example an adenovirus, a pair of initiators allowing us to amplify a target sequence of the genome of the enteric virus in question; or (b) when the enteric virus to be detected is an enteric virus with RNA genome, for example a picornavirus, such as a teschovirus or an enterovirus, a reovirus, such as a rotavirus, an astrovirus, a calicivirus, hepatitis E virus, etc., an initiator allowing us to obtain a cDNA of said enteric virus with RNA genome and/or a pair of initiators allowing us to amplify a target sequence of the cDNA of the enteric virus in question; in a specific embodiment, the enteric virus to be detected is an enterovirus (EV) or a teschovirus and the initiator useful to obtain a cDNA of said EV or said teschovirus is one of the initiators of the pair of initiators that allow us to amplify a target sequence of cDNA of an EV or a teschovirus, respectively; for example, said initiators are specific to RNA regions containing conserved motives shared by EV, such as the initiators identified in this description as SEQ ID NO: 1 and SEQ ID NO: 2, which amplify a 183 bp fragment containing part of the 5'-terminal end of the BEV RNA; in another specific embodiment, the enteric virus to be detected is a teschovirus and the kit provided by the invention contains the initiators identified in this description as SEQ ID NO: 4 and SEQ ID NO: 5.

The kits provided by this invention can be in pack-form containing, besides recipients with the aforementioned or other initiators with the same purpose, recipients with all or part of the other reagents required for the method provided by this invention, for example water, dNTPs (dATP, dCTP, dGTP and dTTP), an appropriate buffer for the reaction (RT, PCR or RT-PCR), a reverse transcriptase, a heat-stable polymerase DNA, a magnesium salt, etc. Additionally and optionally, the kits provided by this invention can include recipients with nucleic acid (RNA, cDNA, DNA, etc.) from an enteric virus such as a teschovirus, an enterovirus, (BEV, for instance), a rotavirus, calicivirus, astrovirus, hepatitis E, an adenovirus, etc., well characterised for use as a positive control.

The following examples illustrate the invention and should not be considered as limiting its scope.

EXAMPLE 1

Identification of the Existence of Environmental Contamination in a Farm with Bovine Livestock 1. Materials and Methods Viruses and cells. The type 2 bovine enterovirus (PS 87 isolate) was obtained from the ATCC (Manassas, Va., USA). The virus was propagated in MDBK (Madin Darbi Bovine Kidney) cells cultivated in Earle's minimum essential medium (MEM) containing 5% of foetal calf serum and antibiotics. The cells were infected at a rate of 1 plate forming units (pfu)/cell and the supernatant containing the viral progeny was collected after 24–36 h, when cytopathic effects were observed in most (>80%) of the single cell layer. The supernatant containing the virus was clarified by centrifugation at 5,000×g for 15 minutes at 4° C. The virus stock was titrated in MDBK cells and stored at 20° C. until use. The BGM kidney cells were supplied by M. A. Jiménez-Clavero (INIA, Madrid—SPAIN).

Collection of faecal samples. The faecal samples were collected directly from the rectums of the bovine livestock (n=138), from the faeces of whitetail deer (*Odocoileus virginianus*) (n=50), and from the faeces of Canadian geese (*Branta canadensis*) (n=4), from pasture land on the Wye Research Farm belonging to the University of Maryland, Queenstown, Md. Approximately 15 g of faeces were suspended in 30 ml of saline phosphate buffer (PBS) for 12 h with occasional agitation. The suspension was centrifuged for 15 minutes at 15,000×g and the supernatant was transferred to a clean test tube. PBS was added to complete a 50 ml volume and its was centrifuged again for 10 minutes at 15,000×g. The supernatants were filtered through a 0.4 µm pore-size membrane, supplemented with antibiotics and stored at −20° C. until they were used. For the deer and geese faeces, after the first centrifugation, the extracts were treated with 5% of chloroform to extract the virus from the organic material, and the tubes were then centrifuged at 10,000×g for 5 minutes and the supernatants were transferred to a clean test tube, filtered through a 0.4 µm pore-size membrane, supplemented with antibiotics and stored at −20° C.

Collection of water samples. The water samples (200 ml) were collected from different parts of the Wye Research Farm and nearby, and from sites next to the Wye river in Queenstown (Md.). Samples WI1 and WI2 were taken from streams flowing from the livestock pastures to the nearby Wye river. Samples WF1, WF2 and WF5 were taken from stagnant ponds in the pastures. Samples WF3 and WF4 were taken from the potable water in the tanks used by the livestock on the farm. The RNA was extracted directly from these water samples, which were not concentrated, as described later. Samples WR1 (Covington Cove), WR2 (Bryan Bar), WR3 (Pintail Point) and WR4 (Bluff's Point) consisted of 50 litres of water collected from different points on the river Wye, approximately 2 km from the coast and approximately 2 m beneath the surface (salinity 14.0 to 15.0 ppt (pars per thousand, that is, g of salt per kg of water); temperature: 4.7° C.–5.8° C.). These water samples were filtered through a 3 µm pore-size membrane (MF, 293 mm diameter, Millipore). The membranes were cut into pieces and the filtrate was recovered by washing the membranes in PBS (5 $cm^2$/ml) for 30 minutes with agitation in vortex. All the samples were stored in sterile test tubes at 4° C. until they were used.

Oyster samples. Oyster (*Crassostrea virginica*) samples were taken from a sand bar on the Wye river, approximately 3 km downstream from the farm. Immediately after they were collected, the oysters were dissected, collecting their stomachs, gills and hemolymph, which were stored in ice until we reached the laboratory. Within 24 hours of being collected, the stomach and gill samples were processed individually. The tissues were cut into small pieces and washed with 5 ml of MEM for 1 h with occasional agitation in vortex. After centrifuging at 1,000×g for 10 minutes, the supernatants were filtered through a 0.4 µm pore-size filter, supplemented with antibiotics and transferred to clean test tubes. All the samples were stored at −20° C. until they were used.

Viral infectivity.

The samples of the faecal extracts and the oysters were added to MDBK cells in plates with 24 or 96 wells (Falcon, Becton Dickinson, Franklin Lake, N.J.), at a final 1:5 dilution (for example, 40 Fl of faecal extract: 160 µl of culture medium). The cultures were kept at 37° C. and 5% $CO_2$ for 2 to 6 days. A cytopathic effect (CPE) was observed in single cell layers between days 2 and 4 of incubation. After 5 days, no new wells with CPE were observed.

The water samples were diluted 1:3 in culture medium and infectivity was determined by the appearance of CPE, as described above.

All the samples that exhibited no CPE in MDBK cells were cultivated in BGM kidney cells, where they also failed to produce CPE.

RNA extraction. The RNA was extracted with a QIAamp Viral RNA mini-kit (Qiagen, Valencia, Calif.). 140 µl of each sample (water, water eluates, oyster washes, faecal extracts or culture supernatants) was processed following the supplier's instructions. The RNA extracted was eluted in 60 µl of RNasa-free water.

Virus detection. An 183 base pair (bp) fragment containing part of the 5'-terminal end of the RNA molecule was amplified to detect BEV RNA with the One-Step RT-PCR Superscript One-Step RT-PCR kit (Gibco BRL, Life Technologies, Grand Island, N.Y., USA). The oligonucleotides were supplied by Gene Probe Technologies, Inc., USA, and included a direct initiator [5'-ACGGAGTAGATGGTAT-TCCC-3'(SEQ ID NO:1), nucleotides 188 to 207], and a reverse initiator [5'-CGAGCCCCATCTTCCAGAG-3'(SEQ ID NO: 2'), nucleotides 389 to 420]. The amplification reaction followed the manufacturer's instructions. The reactions took place in a total volume of 25 µl containing 1× reaction buffer, 0,5 µM of each initiator and 0.5 µl of the DNA Taq polymerase reverse transcriptase enzymatic mix. A total of 6 µl of extracted RNA was tested for each sample. The heat cycle consisted of 50° C. for 30 minutes, 95° C. for 15 minutes and 40 cycles of: 94° C. for 45 s, 56° C. for 45 s, and 72°° C. for 1 minute. A final elongation at 72° C. was performed at the end of each reaction. The reaction products (10 µl) were analysed by electrophoresis in agarose and stained with 0.5 µg/ml of ethidium bromide. Special care was taken to prevent RNA contamination and false positive results. The positive controls were never processed on the same day as the specimens, and the entire RNA extraction process was performed in separate sterile atmospheres.

Sensitivity in BEV detection. Before analysing the samples, the method's sensitivity was measured by introducing known quantities of BEV-2 (PS 87 strain) in a faecal extract free from BEV. The RNA extraction protocol followed by RT-PCR amplification was capable of detecting a quantity of virus corresponding to 0.2–2 pfu in 14 µl of faecal extract, which corresponds to the minimum quantity detected in 3 µg of faeces. This indicates that all the livestock found to be positive by this method has at least 119 pfu/g of faeces. To measure the method's sensitivity to extract RNA from water, known quantities of BEV-2 were added to RNasa-free water and the usual extraction protocol was followed. A positive water sample indicated that the BEV concentration was at least 1.4 pfu/ml of non-concentrated water and approximately 37 pfu/l of filtered water. This estimate refers to the number of infectious particles and not to the quantity of viral RNA molecules, since not all the viral particles in a viral strain are infectious. The limit of detection of the RT-PCR itself was 5–10 copies of the RNA genome.

Sequencing and sequence analyses. The DNA amplification products (15 µl ) obtained after the RT-PCR reactions were purified in gel using a QIAquick PCR purification kit (Qiagen) and sequences with the same initiators used for the amplification. When more than one band was observed, the band corresponding to the correct BEV size was cut, the DNA extracted and purified using the Qiaquick Gel Extraction kit (Qiagen). The sequencing was performed with an ABI PRISM 377 DNA sequencer (Applied Biosystems, Perkin Elmer) or in the Sequencing Service of the Biological Research Centre (Madrid, Spain), using similar equipment. The sequencing analyses were performed using the search and align tools of the EMBL Fasta3 and ClustalW databases, respectively (http://www.ebi.ac.uk/Tools/).

2. Results

BEV in livestock. Faeces from 139 individuals were processed to detect BEV. Of these, 137 samples were taken at the farm itself, in Queenstown, Md., and the other two samples were obtained from livestock housed at the Beltsville Agricultural Research Center Dairy (Beltsville, Md.). These last samples were used as negative controls. The infectivity of all the faecal extracts was examined in MDBK cultures. Infectivity was variable; some extracts were highly cytopathogenic, causing the complete destruction of the single cell layer in two days. Other extracts produced visible CPE after 4 days of culture, and sometimes only a small area of the singe cell layer was affected. Other extracts only produced CPE in one of the duplicate wells, or had results that were not reproducible. The method's sensitivity was compared with that of the plate formation with semi-solid agar protocol using known quantities of pfu of BEV-2, obtaining similar results (not shown). The same levels of sensitivity were obtained in negative faecal samples evaluated with known quantities of BEV-2, indicating that, in these conditions, the faecal extracts did not inhibit cell infection or cell growth. Overall, approximately 40% of the faecal extract samples produced CPE (doubtful results were not included) (Table 1). All the faecal samples that were seen to be infectious in MDBK cells (n=56) and 30 faecal samples that were negative or doubtful were subjected to RNA extraction for the detection of BEV RNA. In this analysis, 76% of the samples were positive (Table 1), resulting in a DNA fragment of the expected size (183 nt). Interestingly, only 51 out of 56 samples that were infectious for the MDBK cells were also RT-PCR positive using BEV initiators. However, 21 of the 39 samples that showed no CPE had a DNA band of the size expected for BEV initiators.

TABLE 1

BEV detection in faecal extracts from livestock

|  | No. of extracts | No. of RT-PCR positive extracts |
|---|---|---|
| CPE + | 56/139 (40.3%) | 51/56 (78%) |
| CPE − | 83/139 (59.7%) | 21/39 (54%) |
| Total | 139 | 72/95 (76%) |

Analysis of BEV in areas potentially contaminated by livestock manure. Since it was determined that most of the livestock was infected with BEV and that the virus was excreted in the faeces, the study was extended to determine if the viral load could contaminate stagnant ponds in the pastures, water in the potable water tanks, the streams flowing through the pastures and the river Wye. The results of this study are shown on Table 2. The two samples (WI1 and WI2) taken from the streams on the farm were positive on both tests: infectivity in cell cultures and RT-PCR. The three water samples taken from the pastures (WF1, WF2, WF5) were positive for BEV by RT-PCR, although only two of them were infectious in MDBK cell cultures (WF2, WF5). One of the two potable water samples taken from the tanks (WF3) was positive for BEV by RT-PCR but no CPE was observed in the cell culture.

TABLE 2

Analysis of BEV in water samples

| Sample | Source | Infectivity | RT-PCR |
|---|---|---|---|
| WI1 | Stream1 | + | + |
| WI2 | Stream 2 | + | + |
| WF1 | Stagnant water in pastures | − | + |
| WF2 | Stagnant water in pastures | + | + |
| WF3 | Potable water on farm | − | + |
| WF4 | Potable water on farm | − | − |
| WF5 | Stagnant water in pastures | + | + |
| RW1 | River Wye (Covington Cove) | − | + |
| RW2 | River Wye (Bryan Bar) | − | − |
| RW3 | River Wye (Pintail Point) | − | − |
| RW4 | River Wye (Bluff's Point) | − | + |

All the water samples from the farm, including the effluents, were positive without the need to concentrate the samples, indicating that the quantity of viral particles was at least 14,000 pfu/l. The samples from the river Wye were negative before they were concentrated and only two samples (RW1 and RW4) were positive by RT-PCR after concentration.

To continue to determine the presence of BEV in the marine environment, we collected 30 oysters from a place on the river from which a water sample (RW1) had been taken. The oyster samples were divided into 3 groups of 10 oysters each and analysed to determine the presence of BEV (Table 3). All the gill wash fractions were infectious for MDBK cells and RT-PCR positive. However, BEV was no detected in any of the hemolymph fractions. Furthermore, the stomach and gills of 5 oysters were analysed individually. BEV was detected in 2 oysters in both tissues, and both of them (the same as another oyster's gill wash water) were infectious in cell cultures. In the positive samples, BEV was only found in gill and/or stomach washes and not in the hemolymph, as per other studies according to which most viral accumulation in molluscs is in the stomach and the diverticulae. Although protocols optimised for virus detection in molluscs have been described, this study used the gill or stomach wash water as the viral source because it is the simplest method, the samples contained no inhibiting substances and the sensitivity was similar to that of optimised protocols (not shown). However, more sensitive methods may be required in less contaminated areas.

TABLE 3

Analysis of BEV in oysters

| Sample | Tissue | CPE | RT-PCR |
|---|---|---|---|
| Pool 1–10 | Hemolymph | − | − |
| Pool 1–10 | Gills | + | + |
| Pool 11–20 | Hemolymph | − | − |
| Pool 11–20 | Gills | + | + |
| Pool 21–30 | Hemolymph | − | − |
| Pool 21–30 | Gills | + | + |
| Oyster 1 | Stomach | − | − |
| Oyster 1 | Gills | − | − |
| Oyster 3 | Stomach | − | − |
| Oyster 3 | Gills | − | +− |
| Oyster 5 | Stomach | − | − |
| Oyster 5 | Gills | − | − |
| Oyster 6 | Stomach | + | + |
| Oyster 6 | Gills | + | + |
| Oyster 8 | Stomach | + | + |
| Oyster 8 | Gills | + | + |

BEV detection in other animals: deer and geese. To determine if other animals, beside the bovine species, could be infected with the virus or act as vectors, we examined 50 faecal extracts from deer and 4 from geese. These animals share the same pastures and the livestock in this study and the faecal samples were collected from these pastures. The samples were processed and analysed for infectivity in MDBK cells and with regards to BEV RNA detection by RT-PCR, in the same way as the bovine samples were treated. As Table 4 shows, 38% (19/50) of the deer samples showed a band of the expected size for the BEV in the RT-PCR analyses.

TABLE 4

BEV detection in faecal extracts from deer

|  | No. of extracts | No. of RT-PCR positive extracts |
| --- | --- | --- |
| CPE + | 28/50 (56%) | 14/50 (28%) |
| CPE − | 22/50 (44.7%) | 5/50 (10%) |
| Total | 50 | 19/50 (38%) |

The reason for examining the geese faeces was that they share the livestock's pastures and can eat seeds and plants contaminated with BEV. Using the same protocol to process these faecal extracts and analyse them to detect BEV, we found that one of every 4 geese faeces was RT-PCR positive for BEV, but not infectious for the MDBK cells (not shown).

Figure 1:
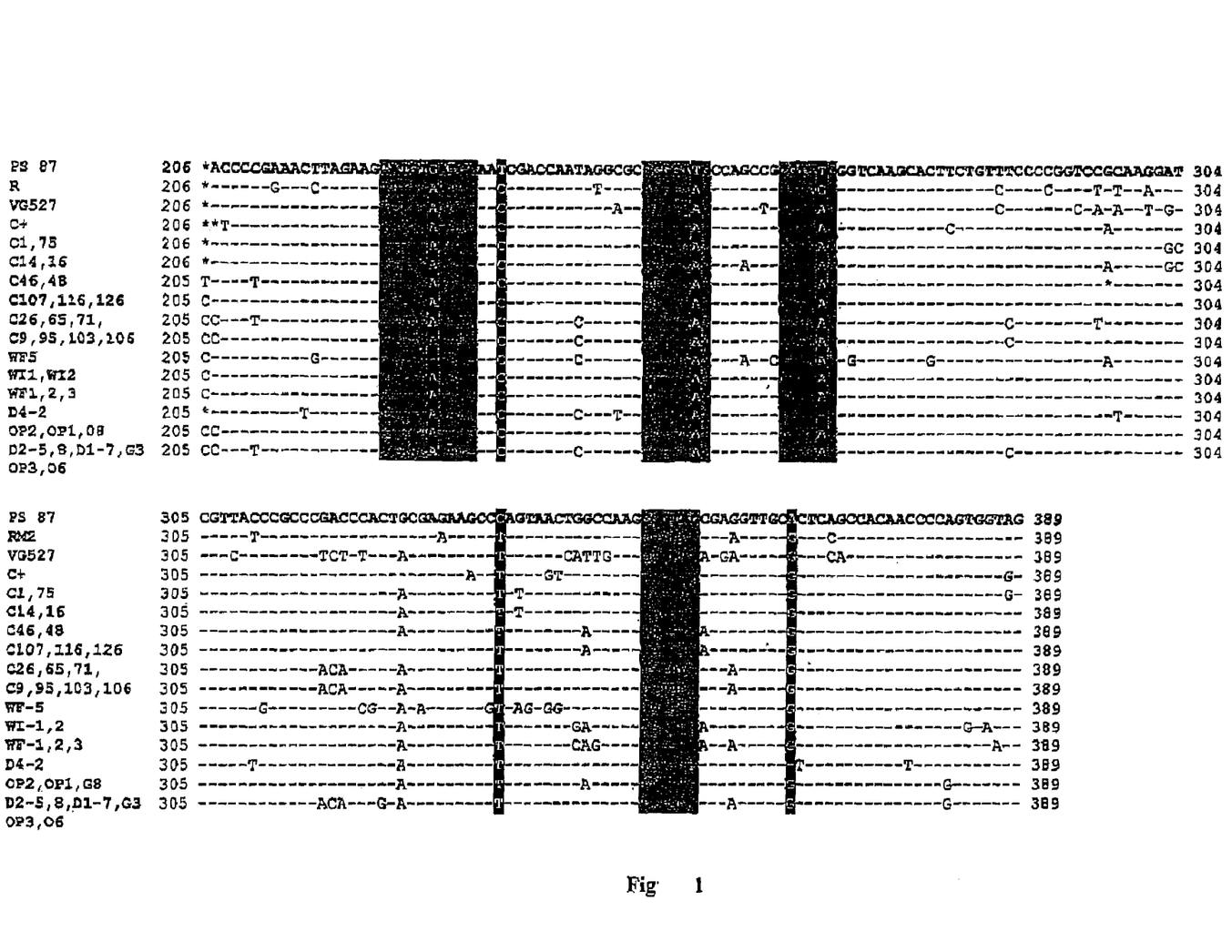
FIG. 1 shows the variability between the 5' NTR sequences of the BEV isolated from bovine faeces. The asterisk (*) corresponds to a deleted nucleotide. C+ corresponds to the sequence of the isolated BEV PS 87 obtained from the ATCC (catalogue number VR-774), used in this invention as a positive control. The numbering of the nucleotides refers to the sequence of the isolated BEV PS 87 (EMBL access number X79368). The sequences of isolated BEV with changes in similar nucleotides have been separated.

Sequence analysis. The aforementioned results show that, in some cases, infectivity in MDBK and amplification by RT-PCR were not correlated. Furthermore, DNA fragments from some specimens, which were amplified with BEV initiators, were not the correct size. In particular, the amplification of fragments of different sizes was relatively frequent in water samples and extracts of deer faeces. This could be due to one or more of the following possibilities: a) the presence of other infectious and cytopathic viruses other than BEV, b) the RT-PCR method is more sensitive that the method to determine infectivity, or c) the presence of other enteroviruses with a RT-PCR product of a size similar to that of the BEV. To investigate these possibilities, we sequenced the amplified DNA fragment of a representative number (n=16) of the 72 livestock faecal samples that were RT-PCR positive for BEV. We also sequences the fragments of the water and oyster samples that had a band of the expected size after amplification, and the positive deer and geese faeces. When we observed more than one amplicon in the agarose gels, the DNA band of the correct size was extracted and used as a sequencing mold. The RT-PCR product was sequenced with the same initiators used for the amplification. The sequences were compared with those published for other BEVs and aligned using the ClustalW programme. As FIG. 1 shows, for the livestock faeces, all the sequences correspond to known BEVs, even those producing no CPE in MDBK cells. This result suggests that the RT-PCR method was more sensitive than the infectivity method in cell cultures and that the quantity of infectious viruses in some faeces was not sufficient to produce detectable CPE in the single cell layer.

All the sequenced samples were more related with BEV strain PS 87 (access number X79368), which has been typified as BEV-2, than with other BEV serotypes. However, they all had some nucleotide changes distinguishing them from PS 87. The same changes have been found in specimens from several livestock species, indicating that they did not correspond to individual mutations but more probably were variants of an original virus. Considering these differences in the nucleotides, the livestock samples could be divided into 3 groups, all of which contained a degree of nucleotide identity of at least 84% in comparison to PS 87.

Figure 2:
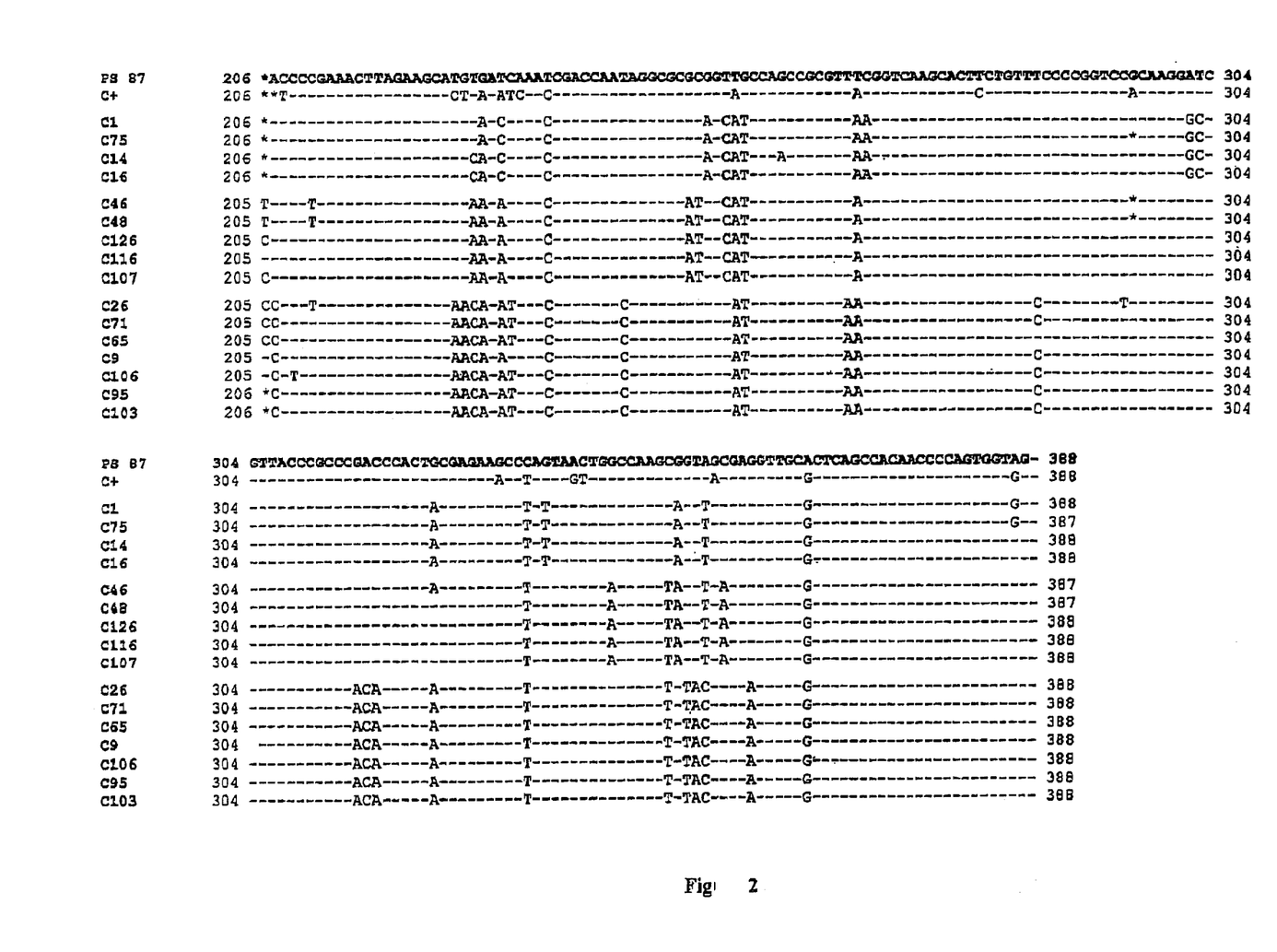

To determine if BEV was contaminating water and oysters, besides deer and geese faeces, and identify the viral chain, we sequences the fragments amplified in the RT-PCR reactions of the RNA extracted from these samples. All the sequences were compared with each other and with the BEV sequences deposited in the EMBL GenBank database. FIG. 2 shows the alignments of the sequences of each livestock group, deer and geese faeces, oysters and water. To simplify the analysis, the sequences in each group are represented by a line. It includes sequences from the same region as the PS 87 (BEV-2), RM2 (BEV-2) and VG527 (BEV-1) serotypes. As with the livestock samples, all the geese, deer, oyster and water sequences corresponded to BEV-2. There are 4 regions with high variability (nt 224–231, 249–256, 267–269 and 349–358). Furthermore, all the samples found in this study had changes in 6 nt, not found in PS 87, but sharing the two RM2 and VG527 isolates. Most of the isolated found in the water samples were similar to livestock samples 46, 48, 107, 116 and 126, whereas most of the deer, geese and oyster samples were similar to livestock samples 26, 65, 71, 9, 95, 103 and 106. These results suggest that the bovine livestock and the deer probably helped to contaminate the aqueous and marine environment with BEV.

3. Discussion

This example describes the first monitoring process of an animal enterovirus (BEV) linked to biological and environmental specimens from the same place. The purpose of this study was firstly to detect BEV in livestock and, if applicable, determine if this virus, which is specific to bovine livestock, was contaminating the environment and could act as a marker of faecal remains of bovine origin.

The high percentage of bovine livestock carrying BEV indicates that this virus is endemic in the area studied. Since large quantities of the BEV are excreted in the infected animals' faeces, we proceeded to examine the presence of this enterovirus in environments potentially affected by the faecal waste from a bovine livestock farm. With this purpose, we analysed several water samples collected from stagnant water in pastures, streams in pastures, potable water in tanks and water and oysters from the adjacent river Wye. The results of the in vitro infectivity and the molecular studies with viral RNA extracted from these samples indicated that these environments were contaminated by BEV. In the water samples collected from stagnant water, streams and tank water, the virus concentration was high enough to be detected without the need for concentration beforehand, with at least 14,000 pfu/l of water. The analyses of the water and oysters from the river Wye confirmed that the marine environment was contaminated with this virus. Two of the four samples of river water and approximately 40% of the oysters contained BEV. Surveillance was complemented with the analysis of 50 faecal samples from deer using the same pastures as the livestock, which could be infected with the virus or act as mechanical vectors. In these analyses, approximately half the deer samples were BEV positive by PCR. These animals also appeared to be the carriers of other pathogens affecting MDBK cells. Since there are a large number of deer in the area and they excrete viral particles in their faeces, they are probably added to the detectable level of enterovirus contaminating the environmental specimens.

To analyse the BEV detected in biological and environmental samples, we sequenced the amplified DNA fragments by RT-PCR using specific BEV initiators. The sequenced region was the 5' NTR region, a region that is highly conserved in many picornaviruses. Although all the sequences studied were more similar to the PS 87 strain of BEV than with other sequences of other BEV strains, significant differences were found between the bovine livestock isolates. In the bovine livestock population, the sequences could be divided into 3 groups, each group had similar and specific nucleotide changes when compared to the PS 87 sequence, but they were all at least 84% similar to this strain. Although the sequence's divergence was relatively low, the region of the viral genome analysed corresponded to a highly conserved region, so a degree of sequence identity of less than 85% in this region could indicate that the isolates could be variants and belong to different serotypes. Since all the samples were taken at the same time in a relatively small area, these results indicate that there are several populations of BEV co-existing in the same area. Viral diversity within this population is remarkably high, even considering the genetic variability of these RNA viruses, and may have interesting implications for viral evolution. The sequencing and analysis of the VP1 region of the viral genome allows us to further characterise these isolated and confirm their serotype.

The analysis of the sequences of samples taken from bovine livestock, deer, water and oysters showed that there were 4 regions in which the largest number of nucleotide changes were found. There were also 6 changes compared to the sequence of the PS 87 strain (GeneBank), which were identical in all the samples and in the BEV RM2 and VG527 isolates, and the BEV isolate used in this study as a positive control (C+). The BEV sequences determined in water samples contained the same variants as those of the livestock groups, heavily suggesting that these animals are the source of contamination. The analysis of the oyster samples indicates that they were contaminated with at least 2 variants of BEV, both found in the livestock population. The analysis of the deer faeces showed that these animals excreted BEV particles in their faeces. However, it is not clear whether the deer are mechanical vectors or susceptible to infection with BEV. The sequence of the 5' NTR region of the deer's BEV isolates was similar to that of a livestock group, except for one deer. Finally, even Canadian geese appear to be carriers of BEV and may contribute to its dissemination from pasture to pasture or from pasture to water.

To summarise, this study indicates that BEV is an endemic virus infecting bovine livestock and, possibly, other ruminants such as deer. The viral population consists of several variants coexisting at the same time in the same area and it is found in the environment associated to bovine livestock. Therefore, BEV can be used as a sensitive marker of faecal contamination of bovine origin.

EXAMPLE 2

Teschoviruses as Indicators of Porcine Faecal Contamination of Water

Teschoviruses specifically infect pigs and are shed in pig faeces. By means of real time quantitative RT-PCR, it is shown here that teschoviruses can be used to specifically determine environmental water contamination caused by spillage of faecal porcine residues from livestock farms. The results correlate with standard methods used to evaluate water contamination.

In this Example, it has been investigated whether the members of the Teschovirus group, a picornavirus genus specific for swine, can be used as indicators of porcine faecal contamination of water. Though originally described as the causative agents of a neurological disorder known as Teschen-Talfan disease [Harding, J. D. J., J. T. Done, and G. F. Kershaw. (1957). Veterinary Record 69:824–832], teschoviruses are generally non-pathogenic, and their infections remain unapparent. This characteristic is frequently found in endemic viruses. Teschoviruses were previously classified as enteroviruses due to the physico-chemical properties of their virions, which are similar to those of enteroviruses. They consist of eleven serotypes, and the nucleotide sequences of most of them have become recently available, the analysis of which has prompted their re-classification into a new picornavirus genus [Carbonell G. et al. (1998). Ecotoxicology and Environmental Restoration 1:85–91; Kaku, Y. et al. (2001). J Gen Virol 82:417–24; Kaku, Y. et al. (1999). Arch Virol 144:1845–52; Krumbholz, A., et al., (2002). J Virol 76:5813–21; Zell, R., et al. (2001). J Virol 75:1620–31]. The data sequence provided in these references was used, in this example, to design primers and a 5'-6'FAM/3'-TAMRA labelled TaqMan probe, targeted at the highly conserved 5' non-coding region (nt 228–295) for a real-time Taq-Man RT-PCR specific for teschoviruses. The oligonucleotide sequence of the TaqMan probe was: 5'-AGC CTA GTA ACA TTC TG-3' [SEQ ID NO: 3] and the oligonucleotide sequences of the primers were: 5'-GTC CGT TAT CCG GCT ACC TAC TT-3' (forward) [4 SEQ ID NO: 4] and 5'-AGC CGC GAC CCT GTC A-3' (reverse) [SEQ ID NO: 5].

Firstly, a specific test to determine porcine teschoviruses (PTV) by quantitative real-time RT-PCR in an ABI Prism 7700 Sequence Detection System, using a standard PTV-1 (isolate Vir 1626/89, kindly provided by Dr. R. Zell. Univ. Jena, Germany) was designed. The virus, propagated in PK-15 cell monolayers, was concentrated and purified by ultracentrifugation of a clarified infection supernatant, for 2 h at 130000×g, through 2 ml 20% sucrose cushion. The viral RNA was isolated using Qiamp Viral RNA mini kit (Qiagen) according to manufacturer's instructions (without RNA carrier) and quantified by $A_{260}$. Dilutions of this viral RNA stock were used as standard to determine PTV RNA in water and faeces samples. The primers (0.5 µM) and the fluorogenic TaqMan probe (0.25 µM) as well as the RT-PCR conditions, were optimised for maximum sensitivity and specificity. The final TaqMan RT-PCR protocol consisted of a first reverse-transcription step at 48° C. for 30 min, followed by 10 min at 95° C. ("hot start") and 50 cycles of 15 sec at 95° C. and 1 min at 60° C. Using the standard PTV-1 RNA, this assay was able to detect 2.8 femtograms of viral RNA, that is, 208 RNA molecules, or $7,4\times10^{-3}$ PTV-1 $TCID_{50}$ per test tube (equivalent to 92 fg/ml non-concentrated supernatant of infection).

To assess whether the assay above described is suitable for the detection of PTV RNA molecules in environmental water and faeces, this TaqMan RT-PCR assay was performed using samples taken from different pig farms and farm environments (Table 5). The samples consisted of sewage water, water from pigsty ponds, and pig slurry. Samples were collected from five pig farms in different locations in Spain, distant at least 50 km apart from each other, in the provinces of Badajoz, Barcelona, and Madrid. Water samples (up to 1.5 l) were tested without any concentration procedure or after concentration by filtration-elution through electropositive filters [Mehnert, D. U., et al. (1997). Mem Inst Oswaldo Cruz 92:97–100]. Negative samples were reanalysed after further concentration by ultracentrifugation at 130.000×g for 2 h at 10° C. RNA was isolated as described above, using 140 µl of water samples or concentrates. The RT-PCR assay was performed as described above. The specificity of the assay was assessed in parallel using aqueous extracts of faeces from cattle, sheep and goats, that were positive for other animal enteroviruses, being completely negative in this analysis (not shown). As shown in Table 5, all pig farms examined resulted positive to PTV RNA, being necessary in some cases, such as APOBA1 and APOBA2, to concentrate the water samples by filtration elution and ultracentrifugation to obtain a positive result.

TABLE 5

Analysis of PTV in water and environmental samples potentially affected from pig faecal contamination

| Farm | nr | Sample | Location | Type of sample | Source | Result | PTV RNA Concentr. Methods |
|------|----|--------|----------|----------------|--------|--------|---------------------------|
| Farm | 1 | APOBA1 | Badajoz | Water | Sewage | + | F/E[a] + UC[b] |
| Farm | 2 | APOBA2 | Badajoz | Water | Pigsty pond | + | F/E[a] + UC[b] |
| Farm | 3 | APOBA3 | Badajoz | Water | Pigsty pond | + | None |
| Farm | 4 | PUOS1 | Barcelona | Pig slurry | Farm soil | + | None |
|      |   | PUOS2 | " | Pig slurry | Farm soil | + | None |
| Farm | 5 | APOJA1 | Madrid | Pig slurry spillage | River | + | None |

Figure 3:
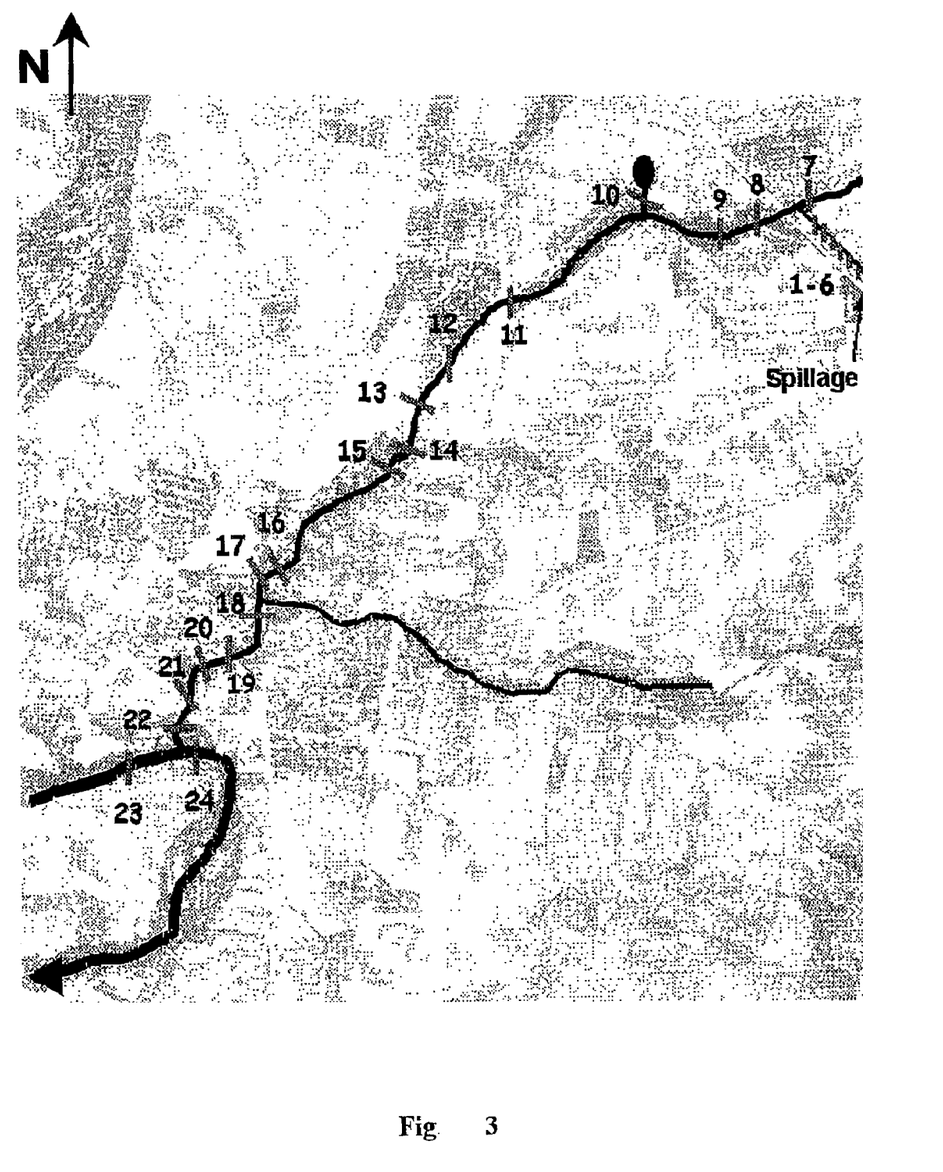
FIG. 3 is a rough map of the area in which the use of teschoviruses as markers of waste contamination of porcine origin was analysed (see Example 2). The water samples were collected and numbered correlatively after spillage of porcine residues.

[a]F/E: water concentrated by filtration-elution
[b]UC: water concentrated by ultracentrifugation To validate this method, 100 ml water samples collected downstream from pig slurry spillage at 24 different points (FIG. 3) were analysed. Samples were collected in the open duct and at different locations in the receiving streams. All samples were analysed physically and chemically in parallel with the PTV RNA quantitative analysis. Sample collection and physico-chemical analysis were performed using standard methods routinely employed at the Laboratory of Ecotoxicology [Tarazona J. V., et al. (1991). Arch. Environ. Contam. Toxicol. 20:480–487] including the analysis of metals by AAS [Carbonell G., et al. (1998). Ecotoxicology and Environmental Restoration 1:85–91]. PTV RNA was quantified by real time RT-PCR TaqMan (described above), using PTV-1 RNA, quantified by $A_{260}$, as standard. The results of both types of determinations were compared and are shown in Table 6.

TABLE 6

Analysis of PTV in water from a river contaminated by pig slurry spillage: comparison with standard parameters of contamination

| Sample nr | Site | PTV RNA (fg/ml) | Organic matter | Nitrates mg/l | Nitrites mg/l | Potassium mg/l | Copper Mg/l |
|-----------|------|-----------------|----------------|---------------|---------------|----------------|-------------|
| OPEN DUCT ||||||||
| 1 | 5 m slurry tank | 578 | 1100 | 7.12 | 2.89 | 1268 | 2.53 |
| 2 | 20 m slurry tank | 1028 | 1120 | 0.93 | 3.02 | 1170 | 2.79 |
| 3 | 40 m slurry tank | 921 | 1110 | 9.63 | 2.61 | 1319 | 4.43 |
| 4 | 100 m slurry tank | 350 | 1120 | 1.48 | 2.47 | 1404 | 2.51 |
| 5 | 150 m slurry tank | 664 | 1260 | 2.73 | 2.71 | 1302 | 2.93 |
| 6 | 200 m slurry tank | 1686 | 2120 | 18.16 | 6.3 | 1398 | 3.45 |
| STREAM ||||||||
| 7 | Upstream | n.d. | 2.61 | 26.87 | 0.05 | 6.91 | 0.007 |
| 8 | 100 m | 6.6 | 4.04 | 137.69 | 0.05 | 6.10 | 0.006 |
| 9 | 500 m | 22.2 | 5.15 | 65.89 | 0.14 | 6.65 | 0.001 |
| 11 | 2000 m | 1.7 | 4.28 | 30.97 | 0.02 | 5.07 | 0.007 |
| 12 | 2500 m | 3.3 | 4.2 | 27.61 | 0.03 | 5.76 | 0.001 |
| 13 | 2800 m | 4.5 | 4.43 | 45.52 | 0.05 | 5.72 | 0.002 |
| 14 | 3000 m | 1.9 | 4.83 | 33.59 | 0.02 | 5.75 | 0.001 |
| 15 | 3100 m | n.d. | 2.3 | 55.09 | 0.04 | 5.75 | 0.004 |
| 16 | 4000 m | n.d. | 2.06 | 61.06 | 0.05 | 2.71 | 0.005 |

TABLE 6-continued

Analysis of PTV in water from a river contaminated by pig slurry spillage: comparison with standard parameters of contamination

| Sample nr | Site | PTV RNA (fg/ml) | Physical-chemical parameters | | | | |
|---|---|---|---|---|---|---|---|
| | | | Organic matter | Nitrates mg/l | Nitrites mg/l | Potassium mg/l | Copper Mg/l |
| 17 | 4100 m | n.d. | 3.09 | 64.91 | 0.02 | 2.76 | 0.004 |
| 18 | 4300 m | n.d. | 2.69 | 33.58 | 0.03 | 3.14 | 0.003 |
| 19 | 4600 m | n.d. | 1.82 | 43.41 | 0.01 | 3.04 | 0.002 |
| 20 | 4800 m | n.d. | 2.45 | 68.72 | 0.03 | 2.12 | 0.000 |
| 21 | 5000 m | n.d. | 3.25 | 38.83 | 0.04 | 3.18 | 0.000 |
| 22 | 5200 m | n.d. | 2.3 | 38.36 | 0.04 | 4.27 | 0.000 |
| | JARAMA RIVER | | | | | | |
| 23 | Upstream | n.d. | 0.63 | n.a | 0.03 | n.a | 0.005 |
| 24 | 2 m downstream (mixing zone) | n.d. | 1.42 | 0.12 | 0.03 | 0.79 | 0.003 |
| | SPRING WATER | | | | | | |
| 10 | 100 m to the stream | n.d. | 1.9 | 54.41 | 0 | 0.99 | 0.002 | n.d. not detectable
n.a not analysed

The results show a high concentration of PTV RNA, consistent with a massive presence of pig slurry, in samples 1–6, collected from a fully contaminated farm open duct, followed by a number of samples collected from the receiving stream, yielding low concentrations of PTV RNA, due to the dilution effect. The PTV RNA becomes undetectable approximately 3100 m downstream from the spillage. Sample 7 was negative, as expected since it was taken a few meters upstream from the point where the stream meets the open duct draining the farm. Sample 10 (also negative) was collected from a spring source 100 m away from the stream, and indicates that the virus did not reach ground waters in detectable amounts at the time the samples were collected.

The physical-chemical analysis confirms no purification in the open duct (samples 1–6). The large differences in the concentration of nitrates can be explained by a combination of oxidation in the surface, and reduction in the waste bulk, confirmed by the significant concentration of nitrites and the absence of dissolved oxygen in the bulk effluent. The waste discharge increases the concentration of organic matter and nitrates in the stream. A rapid oxidation of nitrites to nitrates in the stream is expected considering that dissolved oxygen was over the saturation value in the receiving water. Additional peaks of nitrites and nitrates, were observed several meters downstream from the discharge, as expected by the mineralisation of organic nitrogen [Tarazona, J. V., et al. (1989). Toxicological and Environmental Chemistry 24:9–15]. Nitrates, potassium and copper were already high upstream of the discharge, suggesting additional contamination sources. Pig manure is frequently used as fertiliser in the area, explaining this level of contamination. This hypothesis was in agreement with the analysis of the spring water source, fed by water draining from the same fields as the stream but free from run-off and spillage contamination problems, and showing large levels of nitrates. In the mixing zone, an increase in organic matter was observed, which cannot be explained by a direct organic matter load but by the indirect effect on algal growth associated to the presence of nitrates and other nutrients in the stream.

This example demonstrates that PTVs can be highly sensitive and specific indicators of water contamination due to pig waste. PTV RNA was detected up to three kilometres downstream from the discharge, where the impacts on nitrates and nitrites were no longer observed, and only the unspecific high level of organic matter reflected the upstream discharge. The analytical protocol described in this example can detect specific PTV RNA in amounts as low as 208 viral RNA molecules/test tube, starting from 1.5 l of water. The volume of sample can be increased to up to 10 l without any additional equipment nor essential modifications. Although the prevalence of PTV in pig populations remains to be studied, these results point to a broad distribution, at least in Spain, since the analysed samples came from five points up to 1000 km apart, and all of them resulted positive for PTV RNA.

Example 1 shows that the detection of BEV in surface waters can be useful to monitor water contamination by cattle residues. Example 2 shows that the members of the Teschovirus group can be used as indicators of porcine faecal contamination of water. The same rationale may be applied to the problem of determination of animal waste contamination for any livestock species, given an adequate viral candidate to detect. Optimally, the candidate must fulfil the following characteristics: 1) be specific for the livestock species under consideration; 2) be endemic; 3) be excreted in faeces in detectable amounts; and 4) be stable in the environment. Therefore, provided a suitable animal virus, it is possible to use this approach to determine that a given contamination of water is caused by animal waste.

The invention claimed is:

1. A method for determining the existence of environmental contamination which comprises detecting the presence of a bovine enteric virus in a test sample by an enzymatic amplification reaction of a region of the viral genome of said bovine enteric virus and an analysis of the nucleotide sequence of said amplified region, wherein said amplification is obtained with use of a pair of initiators identified, respectively, as SEQ ID NO:1 and SEQ ID NO:2, and wherein the detection of said bovine enteric virus in said test sample indicates the existence of environmental contamination.

2. The method according to claim 1, wherein said environmental contamination comes from faecal residues of animal origin.

3. The method according to claim 2, comprising:
   a) collecting a test sample for purposes of identifying the existence of environmental contamination by detecting a bovine enteric virus therein;
   b) treating said test sample in conditions which release and extract nucleic acid from the viral particles of bovine enteric viruses present in said test sample;
   c) enzymatically amplifying a sequence of target nucleotides present in the genome of said bovine enteric virus, with the use of said initiators identified, respectively, as SEQ ID NO:1 and SEQ ID NO:2 to obtain an amplification product; and
   d) analyzing said amplification product to determine the presence or absence in said test sample of said bovine enteric virus with the target sequence selected, where the detection of said bovine enteric virus in said test sample indicates the existence of environmental contamination caused by faecal residues of animal origin.

4. The method according to claim 3, wherein said test sample is taken from at least one of a farm, from livestock's drinking water, from the environment surrounding a farm, from environmental specimens, from fish, from molluscs, and from aquatic media in direct or indirect contact with a possible source of contamination.

5. The method according to claim 4, wherein said possible source of contamination is a bovine or porcine livestock farm.

6. The method according to claim 3, wherein said test sample is a test sample liable to contain a bovine enteric virus, selected from a biological test sample and an environmental test sample.

7. The method according to claim 6, wherein said test sample is a biological test sample from an animal, an environmental specimen, a mollusc test sample or a test sample from an aquatic medium.

8. The method according to claim 3, wherein said viral particles are viral particles of bovine enteric viruses having a RNA genome.

9. The method according to claim 8, wherein the extracted RNA is placed into contact with a reaction mix for a reverse transcription reaction (TR) and with a reaction mix for a polymerase chain reaction (PCR) in conditions wherein a sequence of target nucleotides present in the genome of said bovine enteric virus with RNA genome is amplified with the use of said pair of initiators identified, respectively, as SEQ ID NO:1 and SEQ ID NO:2 to form an amplification product.

10. The method according to claim 9, wherein said RT-PCR reaction is performed in a single step or in two steps.

11. The method according to claim 9, wherein said reaction mix used to perform the reverse transcription (RT) of the RNA of said bovine enteric virus contains said pair of initiators.

12. The method according to claim 9, wherein said reaction mix used to perform the PCR contains said pair of initiators.

13. The method according to claim 3, wherein said viral particles are viral particles of bovine enteric viruses having a DNA genome.

14. The method according to claim 13, wherein the extracted DNA is placed into contact with a reaction mix for a polymerase chain reaction (PCR) in conditions wherein a target sequence of nucleotides present in the genome of said bovine enteric virus having a DNA genome is amplified to form an amplification product with the use of said pair of initiators.

15. The method according to claim 14, wherein said PCR reaction is performed in a single step or in two steps.

16. The method according to claim 14, wherein said reaction mix for the PCR comprises said pair of initiators for amplifying the target sequence of the genome of said bovine enteric virus.

17. The method according to claim 3, wherein said amplification product is separated by electrophoresis in agarose and viewed with ultraviolet light after staining with ethidium bromide.

18. A method for locating the origin of a source of environmental contamination by detecting a bovine enteric virus in a test by an enzymatic amplification reaction of a region of the viral genome and an analysis of its nucleotide sequence, wherein said amplification is obtained with a pair of initiators identified as, respectively, SEQ ID NO:1 and SEQ ID NO: 2, and comparing enteric viruses eventually detected in said test sample with other enteric viruses isolated and characterised in different possible sources of contamination, where the existence of a certain degree of identity between the isolated of the enteric viruses detected and characterised in said test sample and the isolated of the enteric viruses found in a possible source of contamination indicates that said possible source of contamination is the source of environmental contamination.

19. The method according to claim 18, wherein said source of environmental contamination is a source of faecal contamination of animal origin.

20. The method according to claim 19, wherein the comparison of the enteric viruses detected in said test sample and the enteric viruses isolated and characterised in different possible sources of contamination, is performed by sequencing studies or molecular typification or serological studies.

21. The method according to claim 19, wherein the degree of identity between the isolates of bovine enteric viruses detected and characterized in said test sample and the isolates of bovine enteric viruses isolated in said possible source of contamination is 50% or more, and wherein said degree of identify is determined by molecular sequencing.

22. A kit for the detection of bovine enteric viruses as environmental contamination markers by ehzymatic amplification, said kit comprising:
   (a) when the enteric virus to be detected is an enteric virus having a DNA genome, a pair of initiators identified, respectively, as SEQ ID NO:1 and SEQ ID NO:2, for allowing the amplification of a target sequence of the genome of the enteric virus in question; or
   (b) when the enteric virus to be detected is an enteric virus having a RNA genome, an initiator for obtaining a cDNA of said enteric virus having an RNA genome and/or said pair of initiators identified, respectively, as SEQ ID NO:1 and SEQ ID NO:2 for amplifying a target sequence of the cDNA of the enteric virus in question.

23. The kit according to claim 22, for the detection of a bovine enteric virus having an RNA genome by RT-PCR, said kit comprising said initiator for obtaining a cDNA of said bovine enteric virus, and/or said pair of initiators identified, respectively as SEQ ID NO:1 and SEQ ID NO:2 for allowing amplifying said target sequence of the cDNA of said enteric virus.

24. The kit according to claim 23, wherein said initiator useful for obtaining a cDNA of said bovine enteric virus having a RNA genome is selected from the group consisting of SEQ ID NO:1 and SEQ ID NO:2.

25. The method according to claim 21, wherein the degree of identity between the isolates of bovine enteric viruses detected and characterized in said test sample and the isolates of bovine enteric viruses isolated in said possible source of contamination is 80% or more.

26. The method according to claim 21, wherein the degree of identity between the isolates of bovine enteric viruses detected and characterized in said test sample and the isolates of bovine enteric viruses isolated in said possible source of contamination is 95% or more.

* * * * *

UNITED STATES PATENT AND TRADEMARK OFFICE
CERTIFICATE OF CORRECTION

PATENT NO. : 7,122,315 B2  Page 1 of 1
APPLICATION NO. : 10/370927
DATED : October 17, 2006
INVENTOR(S) : Victoria Ley Vega De Seoane et al.

It is certified that error appears in the above-identified patent and that said Letters Patent is hereby corrected as shown below:

On the Title Page item (75), should read:
Victoria Ley Vega De Seoane, Madrid, Spain
Miguel Angel Jimenez Clavero, Madrid, Spain
Ronald Fayer, Ellicott City, MD
James A. Higgins, Jessup, MD Signed and Sealed this Fifth Day of August, 2008

JON W. DUDAS
*Director of the United States Patent and Trademark Office*

SEQUENCE LISTING

<160> NUMBER OF SEQ ID NOS: 5

<210> SEQ ID NO 1
<211> LENGTH: 20
<212> TYPE: DNA
<213> ORGANISM: Artificial
<220> FEATURE:
<223> OTHER INFORMATION: Forward oligonucleotide initiator

<400> SEQUENCE: 1
acggagtaga tggtattccc					20

<210> SEQ ID NO 2
<211> LENGTH: 19
<212> TYPE: DNA
<213> ORGANISM: Artificial
<220> FEATURE:
<223> OTHER INFORMATION: Reverse Oligonucleotide initiator

<400> SEQUENCE: 2
cgagccccat cttccagag					19

<210> SEQ ID NO 3
<211> LENGTH: 17
<212> TYPE: DNA
<213> ORGANISM: Artificial
<220> FEATURE:
<223> OTHER INFORMATION: Sequence of nucleotides from the Taqman probe

<400> SEQUENCE: 3
agcctagtaa cattctg					17

<210> SEQ ID NO 4
<211> LENGTH: 23
<212> TYPE: DNA
<213> ORGANISM: Artificial
<220> FEATURE:
<223> OTHER INFORMATION: Forward oligonucleotide initiator

<400> SEQUENCE: 4
gtccgttatc cggctaccta ctt					23

<210> SEQ ID NO 5
<211> LENGTH: 16
<212> TYPE: DNA
<213> ORGANISM: Artificial
<220> FEATURE:
<223> OTHER INFORMATION: Reverse oligonucleotide initiator

<400> SEQUENCE: 5
agccgcgacc ctgtca					16